(12) United States Patent
Lavigne et al.

(10) Patent No.: US 11,896,762 B2
(45) Date of Patent: Feb. 13, 2024

(54) ENDOTRACHEAL TUBE SYSTEM AND METHOD FOR MAINTAINING AIRWAY PATENCY

(71) Applicant: Avent, Inc., Alpharetta, GA (US)

(72) Inventors: Mark Lavigne, Boston, MA (US); Edward B. Madsen, Cumming, GA (US)

(*) Notice: Subject to any disclaimer, the term of this patent is extended or adjusted under 35 U.S.C. 154(b) by 859 days.

(21) Appl. No.: 16/856,205

(22) Filed: Apr. 23, 2020

(65) Prior Publication Data

US 2021/0330917 A1 Oct. 28, 2021

(51) Int. Cl.
*A61M 16/04* (2006.01)
*A61M 16/06* (2006.01)
*A61M 39/16* (2006.01)

(52) U.S. Cl.
CPC .... *A61M 16/0463* (2013.01); *A61M 16/0688* (2014.02); *A61M 39/16* (2013.01); *A61M 2202/203* (2013.01); *A61M 2209/10* (2013.01)

(58) Field of Classification Search
CPC ........ A61M 16/04–0497; A61M 39/16; A61M 2025/0183; A61M 2025/09175; A61M 2025/09183; A61M 2039/087; A61M 2039/1066; A61M 2202/203; A61M 2209/04; A61M 2209/10; A61B 1/00142; A61B 1/126; A61B 2017/00336; A61B 2017/0034; A61B 2017/00349;
(Continued)

(56) References Cited

U.S. PATENT DOCUMENTS 4,502,482 A * 3/1985 DeLuccia ......... A61M 16/0463
  128/207.14
6,134,111 A 10/2000 Mongeon
(Continued)

FOREIGN PATENT DOCUMENTS

CN 107281605 A 10/2017
WO WO 2004/101048 A2 11/2004
(Continued)

OTHER PUBLICATIONS

International Search Report and Written Opinion for PCT/US2021/028628, dated Aug. 9, 2021, 17 pages.

*Primary Examiner* — Valerie L Woodward
(74) *Attorney, Agent, or Firm* — Sheridan Ross P.C.

(57) ABSTRACT

An endotracheal tube airway patency system and method are provided. The system includes an endotracheal tube having a tube body having a proximal end, a distal end, an inner surface, a distal opening disposed at the distal end of the tube body, a proximal opening disposed at the proximal end of the tube body, and an airflow-effacing surface disposed within the tube body. The airflow-effacing surface includes a telescoping inner sleeve configured to be removed from the endotracheal tube body. The system further includes a tool for removal of the telescoping internal sleeve from the endotracheal tube body. The tool includes an elongated body having a proximal end and a distal end; a handle located at the proximal end of the elongated body; and at least one extension member disposed at the distal end of the elongated body. The at least one extension member is configured to couple to the telescoping internal sleeve for removal of the telescoping internal sleeve from the endotracheal tube body.

14 Claims, 4 Drawing Sheets

(58) Field of Classification Search
CPC .. A61B 2017/0096; A61B 2017/00995; A61B 2017/12086
See application file for complete search history.

(56) References Cited

U.S. PATENT DOCUMENTS

| | | | |
|---|---|---|---|
| 6,257,236 B1* | 7/2001 | Dutkiewicz | A61M 16/06 128/207.14 |
| 7,051,737 B2 | 5/2006 | Kolobow et al. | |
| 8,157,919 B2 | 4/2012 | Vazales et al. | |
| 8,381,345 B2 | 2/2013 | Vazales et al. | |
| 8,382,908 B2 | 2/2013 | Vazales et al. | |
| 8,458,844 B2 | 6/2013 | Vazales et al. | |
| 8,468,637 B2 | 6/2013 | Vazales et al. | |
| 8,534,287 B2 | 9/2013 | Vazales et al. | |
| 8,601,633 B2 | 12/2013 | Vazales et al. | |
| 9,095,286 B2 | 8/2015 | Vazales et al. | |
| 9,332,891 B2 | 5/2016 | Vazales et al. | |
| 9,386,907 B2 | 7/2016 | Vazales et al. | |
| 9,398,837 B2 | 7/2016 | Vazales et al. | |
| 9,445,714 B2 | 9/2016 | Vazales et al. | |
| 9,579,012 B2 | 2/2017 | Vazales et al. | |
| 9,821,130 B2 | 11/2017 | Schumacher et al. | |
| 9,855,111 B2 | 1/2018 | Vazales et al. | |
| 9,907,624 B2 | 3/2018 | Vazales et al. | |
| 9,962,233 B2 | 5/2018 | Vazales et al. | |
| 10,004,863 B2 | 6/2018 | Vazales et al. | |
| 10,016,575 B2 | 7/2018 | Vazales et al. | |
| 10,441,380 B2 | 10/2019 | Vazales et al. | |
| 2010/0106236 A1* | 4/2010 | Nelson | A61M 25/00 128/207.14 |
| 2010/0199999 A1* | 8/2010 | Vazales | A61B 90/70 128/207.14 |
| 2011/0083672 A1* | 4/2011 | Webster | A61M 16/0427 128/207.15 |
| 2011/0197894 A1 | 8/2011 | Morejon | |
| 2012/0174920 A1* | 7/2012 | Barkai | A61M 16/04 128/200.26 |
| 2014/0378792 A1* | 12/2014 | Krimsky | A61L 2/10 128/200.26 |
| 2017/0258550 A1 | 9/2017 | Vazales | |
| 2018/0228571 A1 | 8/2018 | Vazales | |
| 2019/0046751 A1 | 2/2019 | Vazales et al. | |
| 2019/0060606 A1 | 2/2019 | Vazales et al. | |
| 2019/0151587 A1 | 5/2019 | Vazales et al. | |
| 2019/0336714 A1 | 11/2019 | Vazales et al. | |
| 2020/0046453 A1 | 2/2020 | Vazales et al. | |

FOREIGN PATENT DOCUMENTS

| | | | | |
|---|---|---|---|---|
| WO | WO 2010/091309 A1 | 8/2010 | | |
| WO | WO 2019/234749 A1 | 12/2019 | | |
| WO | WO-2019234749 A1 * | 12/2019 | | A61B 90/70 |

* cited by examiner

ENDOTRACHEAL TUBE SYSTEM AND METHOD FOR MAINTAINING AIRWAY PATENCY

FIELD OF THE INVENTION

The subject matter of the present invention relates generally to respiratory care systems for intubated patients, and more specifically to an endotracheal tube having a telescoping internal sleeve and a tool for removing the internal sleeve.

BACKGROUND

Endotracheal tubes are essential elements of the critical care armamentarium to bridge the gap between patient fragility and independent, healthy living. Ironically, however, it is in patients' best interests to discontinue use of this lifesaving apparatus as soon as possible, because phenomena affect in-use endotracheal tubes that can prolong a patient's dependence on mechanical ventilation and exacerbate their illness(es). In particular, deposition of pathogenic microorganisms, biofilm, and/or secretions can occlude an endotracheal tube, thereby increasing a patient's work of breathing, placing more stress on a patient in an already-fragile state, and thus potentially extend the duration of mechanical ventilation. The second ominous possibility posed by microbial or biofilm presence in an endotracheal tube is the development of ventilator-associated pneumonia, which is a lung infection that develops in a patient who is on a ventilator. Ventilator-associated pneumonia has an associated mortality of up to 40%. Thus, it is of paramount importance to keep in-use endotracheal tubes as clear as possible of secretions and microbial or biofilm deposits.

Several methodologies are currently available to maintain or restore in-use patency of an in-use endotracheal tube. Closed and open suctioning techniques can be effective to remove loose secretions from the inside of an endotracheal tube, while mechanical wiping or scrubbing methods, which may use balloons to wipe or scrape the inner, airflow-effacing layer of an endotracheal tube, are theoretically useful for removing sticky secretions and microbial or biofilm deposits physically stuck to the endotracheal tube. However, various pitfalls of these technologies have been revealed by peer-reviewed studies, including that suctioning alone does not adequately maintain proper endotracheal tube function and can instead worsen physiological, especially cardiorespiratory, patient markers (i.e., open suctioning). Similarly, wiping technologies fail to remove all occlusive substances in endotracheal tubes. Moreover, because the operation of mechanical wiping methods interrupts the ventilation circuit by blocking some or all of the airflow through the tube, such methods can adversely affect patient cardiorespiratory function. Even very small changes to the diameter of the ventilating lumen of an endotracheal tube, e.g., vey small occlusions within the lumen, can significantly increase airflow resistance, and thereby, increase the patient's work of breathing. This is because, as predicted by Poiseulle's law, changes in airflow vary directly according to the 4th power of the luminal radius. Thus, for example, a 50% (one half or ½) reduction in the diameter of the ventilating lumen increases endotracheal tube airflow resistance by a factor of sixteen (16). Furthermore, mechanical disruption of biofilm imposed by wiping or scrubbing may splinter biofilm such that some of it could embolize, i.e., escape being captured by suctioning and/or wiping, and instead enter a lung to initiate infection. The tenuous benefit-to-risk ratios of these endotracheal tube-clearing techniques suggest the need for an alternative strategy to more safely keep an endotracheal tube as clear and clean as possible while being used to facilitate mechanical ventilation.

Consequently, there is a need for a solution to maintain endotracheal tube patency and remove microbial or biofilm secretions from an in-use endotracheal tube. In particular, a solution to clear the airway of an in-use endotracheal tube while minimally impacting the airflow through the tube would also be useful.

SUMMARY

The present invention is directed to a tool for removal of a telescoping internal sleeve from an endotracheal tube. The tool includes an elongated body having a proximal end and a distal end. The tool also includes a handle located at the proximal end of the elongated body. The tool further includes at least one extension member disposed at the distal end of the elongated body. The at least one extension member is configured to couple to the telescoping internal sleeve of the endotracheal tube for removal of the telescoping internal sleeve from the endotracheal tube.

In one particular embodiment of the tool, the at least one extension member can include three extension members.

In another embodiment of the tool, the handle can include a dial configured to rotate, wherein rotation of the dial in a first direction causes the at least one extension member to be moved into an open position and wherein rotation of the dial in a second direction causes the at least one extension member to be moved into a closed position. Moreover, in the open position, the at least one extension member can be configured to initiate coupling to the telescoping internal sleeve. Furthermore, when the dial is rotated from the open position to the closed position, the at least one extension member can be configured to retain the telescoping internal sleeve to retract the telescoping internal sleeve from the endotracheal tube.

In an additional embodiment, the at least one extension member can include a hook extending from a distal end of the at least one extension member. Moreover, the tool can further include a protrusion extending from the distal end of the at least one extension member, wherein the hook extends from the protrusion. Furthermore, the hook can be configured to couple to a receiving tab of the telescoping internal sleeve. Additionally or alternatively, the hook can include a magnetic hook.

In one more embodiment, the at least one extension member can include a coupler disposed at a distal end of the at least one extension member. Moreover, the coupler can include a magnetic attachment configured to couple to a magnetic receiving tab of the telescoping internal sleeve. Furthermore, the coupler can include an adhesive attachment.

The present invention is further directed to an endotracheal tube airway patency system. The system includes an endotracheal tube having a tube body having a proximal end, a distal end, an inner surface, a distal opening disposed at the distal end of the tube body, a proximal opening disposed at the proximal end of the tube body, and an airflow-effacing surface disposed within the tube body, wherein the airflow-effacing surface comprises a telescoping inner sleeve configured to be removed from the endotracheal tube body. The system further includes a tool for removal of a telescoping internal sleeve from the endotracheal tube body. The tool includes an elongated body having a proximal end and a distal end; a handle located at the proximal end of the elongated body; and at least one extension member disposed at the distal end of the elongated body. The at least one extension member is configured to couple to the telescoping internal sleeve for removal of the telescoping internal sleeve from the endotracheal tube body.

In one particular embodiment of the endotracheal tube airway patency system, the telescoping inner sleeve can include one or more layers which are independently removable from the endotracheal tube body.

In another embodiment, the telescoping inner sleeve can include at least one receiving tab configured to be coupled with the at least one extension member of the tool.

In an additional embodiment, the telescoping inner sleeve can be collapsible.

In a further embodiment, the telescoping inner sleeve can be disposed adjacent to or in contact with the inner surface of the endotracheal tube body to maintain patency of the endotracheal tube.

In one more embodiment, removal of the telescoping inner sleeve can expose a sterile surface on the inner surface of the endotracheal tube body.

The present invention is further directed to a method of maintaining patency and removing deposits from an endotracheal tube. The method includes a step of providing an endotracheal tube having a tube body having a proximal end, a distal end, an inner surface, a distal opening disposed at the distal end of the tube body, a proximal opening disposed at the proximal end of the tube body, and an airflow-effacing surface disposed within the tube body, wherein the airflow-effacing surface comprises a telescoping inner sleeve configured to be removed from the endotracheal tube body. The method further includes a step of providing a tool for removal of a telescoping internal sleeve from the endotracheal tube body. The tool includes: an elongated body having a proximal end and a distal end; a handle located at the proximal end of the elongated body; and at least one extension member disposed at the distal end of the elongated body, wherein the at least one extension member is configured to couple to the telescoping internal sleeve for removal of the telescoping internal sleeve from the endotracheal tube body. The method further includes a step of inserting the tool into the endotracheal tube body. The method further includes a step of using the tool to retrieve and remove the telescoping inner sleeve from the endotracheal tube body.

In one particular embodiment of the method, the steps of inserting the tool into the endotracheal tube body and using the tool to retrieve and remove the telescoping inner sleeve from the endotracheal tube body can be performed without interrupting an active mechanical ventilation circuit.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
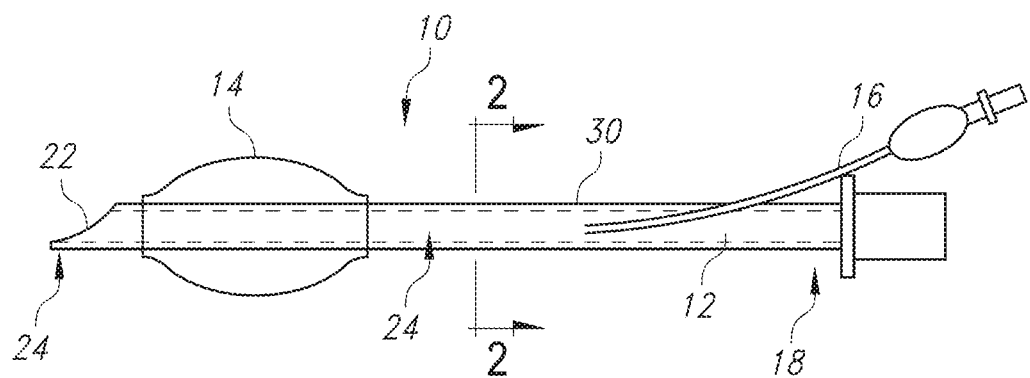
FIG. 1 illustrates a side view of an endotracheal tube having a telescoping inner sleeve according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to an endotracheal tube airway patency system and method. The system includes an endotracheal tube having a tube body having a proximal end, a distal end, an inner surface, a distal opening disposed at the distal end of the tube body, a proximal opening disposed at the proximal end of the tube body, and an airflow-effacing surface disposed within the tube body. The airflow-effacing surface includes a telescoping inner sleeve configured to be removed from the endotracheal tube body. The system further includes a tool for removal of the telescoping internal sleeve from the endotracheal tube body. The tool includes an elongated body having a proximal end and a distal end; a handle located at the proximal end of the elongated body; and at least one extension member disposed at the distal end of the elongated body. The at least one extension member is configured to couple to the telescoping internal sleeve for removal of the telescoping internal sleeve from the endotracheal tube body.

The use of a removable sleeve within an endotracheal tube, and a tool specially configured for removal of the sleeve from the endotracheal tube without breaking the mechanical ventilation circuit, may provide an improved way to remove the buildup of microorganisms, biofilm and/or secretions from the interior of an endotracheal tube, thereby exposing a fresh, undisturbed, uncontaminated and potentially sterile airflow-effacing surface without blocking or interrupting the airflow of ventilation when the endotracheal tube is in use. As a result, the endotracheal tube system of the present invention may be able to prolong the amount of time that the tube can remain safely intubated within a patient for mechanical ventilation by reducing the threat of the endotracheal tube being compromised by occlusion and/or colonization by microorganisms, biofilm and/or secretions that could cause infection. At the same time, by reducing the likelihood of occlusion of the ventilating lumen by removing the telescoping inner sleeve to reveal a virgin inner surface, the endotracheal tube system of the present invention may improve the chances for a patient to pass a breathing trial, and thus be alleviated from their dependence on mechanical ventilation, by providing an in-use endotracheal tube that can remain as clear as a tube that has never been used (i.e., never had any buildup of secretions, biofilms, etc.).

The specific features of the endotracheal tube system and method of the present invention may be better understood with reference to FIGS. 1-10.

Referring now to FIG. 1, one embodiment of an endotracheal tube 10 in accordance with the present invention is shown. The endotracheal tube 10 includes a tube body 12 extending from a proximal end 18 to a distal end 20. The tube body 12 includes a distal opening 22 at the distal end 20. The tube body 12 includes a ventilating lumen 24 defined by the inner surface 26 of the tube body 12 that runs the entire length of the tube body 12 from the proximal end 18 to the distal opening 22 at the distal end 20 in order to deliver breathing air to the patient. The endotracheal tube 10 also includes a balloon 14 mounted to the tube body 12 adjacent to the distal end 20. The endotracheal tube 10 also includes an inflation line 16 in fluid communication with and used to inflate the balloon 14 in order to expand the balloon 14 to seal the patient's airway.

Polymers suitable for the production of the endotracheal tube 10 include polyvinyl chloride, polyurethane and polyolefins such as polyethylene and polypropylene. Nylons and polyethylene terephthalate (PET) materials may also be used. Blends of suitable polymers may also be used. It is also possible using known extrusion techniques to extrude parts of the endotracheal tube 10 from one polymer and other parts of the endotracheal catheter from other polymers. For example, the inner surface 26 or ventilating lumen 24 wall may be made of a first polymer such as polyvinyl chloride and an outer wall of the tube body 12 may be made from a second polymer such as polyurethane. A material having antimicrobial properties, such as polyurethane formulated to have antimicrobial properties, may also be ideal for forming the tube body 12.

Figure 2:
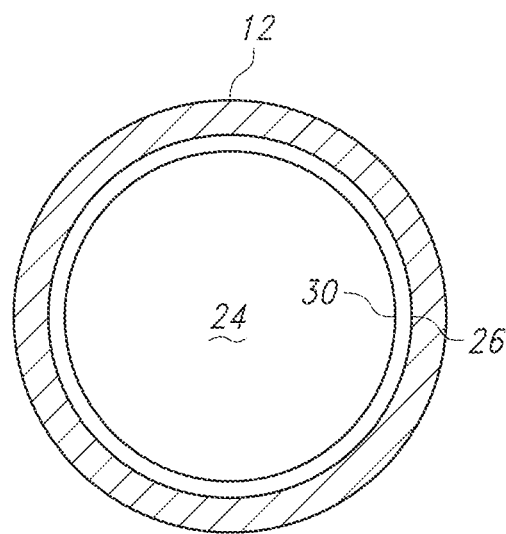
FIG. 2 illustrates a cross-sectional view of the endotracheal tube of FIG. 1 taken along line 2-2 of FIG. 1.

The endotracheal tube 10 of the present invention may further include at least one telescoping internal sleeve 30 disposed within the tube body 12, as shown in FIGS. 1 and 2. The at least one telescoping internal sleeve 30 is configured to be axially disposed adjacent to the inner surface 26 of the tube body 12 such that the ventilating lumen 30 is defined within the interior of the at least one telescoping internal sleeve 30. The at least one telescoping internal sleeve 30 is configured to be an airflow-effacing liner that can be removed from the interior of the endotracheal tube 10. When the at least one telescoping internal sleeve 30 is removed, a sterile inner surface, such as the inner surface 26 of the tube body 12, is exposed to continue mechanical ventilation. In some aspects of the invention, the endotracheal tube 10 can include a plurality of telescoping inner sleeves 30 serially disposed within each other and surrounding the ventilating lumen 24. For instance, there can be two telescoping inner sleeves 30 in an endotracheal tube 10.

The at least one telescoping internal sleeve 30 can be formed from a material that is flexible to be removed from within the endotracheal tube 10 while being sufficiently rigid to maintain the open ventilating lumen 24, as shown in FIG. 2, and not collapse or block the lumen 24 during removal of the sleeve 30. For instance, the at least one telescoping internal sleeve 30 can be formed from polyurethane. Polyurethane offers high elongation values (i.e., stretchability) like rubber, and abrasion resistance superior to that of PVC. A material having antimicrobial properties, such as polyurethane formulated to have antimicrobial properties, would also be ideal for forming the telescoping internal sleeve 30. The at least one telescoping internal sleeve 30 can have a thickness as small as about 0.05 millimeters or about 0.002 inches. The at least one telescoping internal sleeve 30 can have a thickness up to a thickness that does not interfere with the patency of the tube 12, such as a thickness of about 0.75 millimeters or about 0.03 inches. For instance, the thickness of the telescoping internal sleeve 30 can be in a range of from about 0.05 millimeters to about 0.75 millimeters, or from about 0.002 inches to about 0.030 inches. The thickness of the at least one telescoping internal sleeve 30 may be minimized in order to maximize the radius of the ventilating lumen 24 in order to reduce any potential increase in airflow resistance within the ventilating lumen 24.

When in use, an endotracheal tube such as the endotracheal tube 10 of the present invention may accumulate pathogenic microorganisms, biofilm, and/or secretions on the airflow-effacing surface within the tube body 12. By utilizing at least one removable telescoping internal sleeve 30 within the endotracheal tube 10, layers of an in-use endotracheal tube airflow-effacing surface formed by each telescoping internal sleeve 30 can be serially removed. When each telescoping internal sleeve 30 is removed, the airflow-effacing surface of the telescoping internal sleeve 30 which may have buildup of microorganisms, biofilm and/or secretions is removed, thereby exposing a fresh, undisturbed, uncontaminated and potentially sterile airflow-effacing surface. Thus, the inner airflow-effacing surface of the endotracheal tube 10 can be cleared of any buildup of microorganisms, biofilm and/or secretions without blocking or interrupting the airflow of ventilation when the endotracheal tube 10 is in use. As a result, the endotracheal tube 10 of the present invention may be able to prolong the amount of time that the tube can remain safely intubated within a patient for mechanical ventilation by reducing the threat of the endotracheal tube being compromised by occlusion and/or colonization by microorganisms, biofilm and/or secretions that could cause infection. At the same time, by reducing the likelihood of occlusion of the ventilating lumen 24 by removing the telescoping inner sleeve 30 to reveal a virgin inner surface 26, the endotracheal tube 10 of the present invention may improve the chances for a patient to pass a breathing trial, and thus be alleviated from their dependence on mechanical ventilation, by providing an in-use endotracheal tube that can remain as clear as a tube that has never been used (i.e., never had any buildup of secretions, biofilms, etc.).

In order to remove the telescoping internal sleeve 30 from the endotracheal tube 10 while the tube is in-use, i.e., intubated in a patient and actively providing mechanical ventilation, the sleeve 30 must be removed without breaking the ventilation circuit. In some aspects, the endotracheal tube 10 can be used in conjunction with a multi-access port (not shown), such as a multi-access port that facilitates a closed-suction system for an endotracheal tube, to introduce a tool for removing the telescoping inner sleeve 30 into the endotracheal tube 10 for removal of the sleeve 30. However, any mechanism by which the telescoping inner sleeve 30 can be removed without breaking the ventilation circuit may be used.

Figure 6:
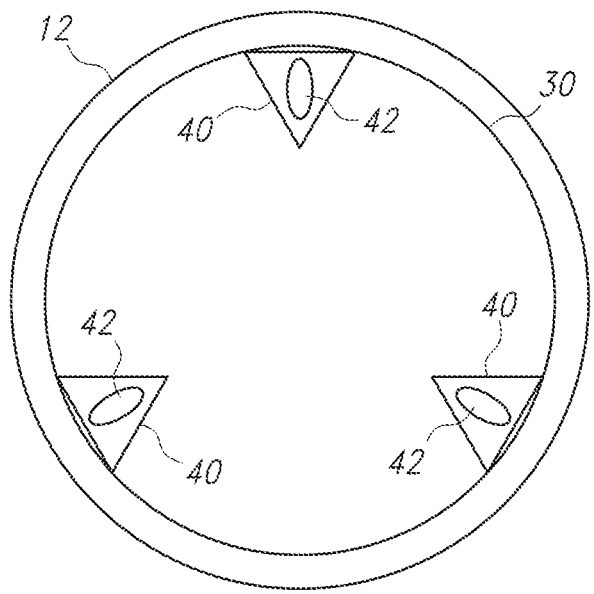
FIG. 6 illustrates a cross-sectional view of the endotracheal tube of FIG. 1 having a telescoping inner sleeve with receiving tabs.

The telescoping internal sleeve 30 can have one or more receiving features by which the sleeve 30 can be retrieved. For instance, as shown in FIG. 6, the sleeve 30 can include one or more receiving portions 40. Each receiving portion 40 can include an aperture 42 through which a retrieval tool, e.g., a hook, may be received. The sleeve 30 can include one singular receiving portion 40, or two or more receiving portions 40, such as three receiving portions 40 as shown in FIG. 6. In some aspects, the number of receiving portions 40 on the sleeve 30 can correspond to a number of hooks and/or other retrieval tools configured to retrieve the sleeve 30 and remove the sleeve 30 from the endotracheal tube 10. In other aspects, the at least one receiving portion 40 may not include an aperture 42. Additionally or alternatively, the at least one receiving portion 40 may include one or more features configured to couple with a tool configured for retrieving and removing the sleeve 30 from the endotracheal tube 10. For instance, the one or more coupling features may include one or more magnets, adhesive portions, clips, fasteners, or any other suitable feature by which the receiving portion 40 could be coupled to a tool in order to remove the sleeve 30.

Figure 5A:
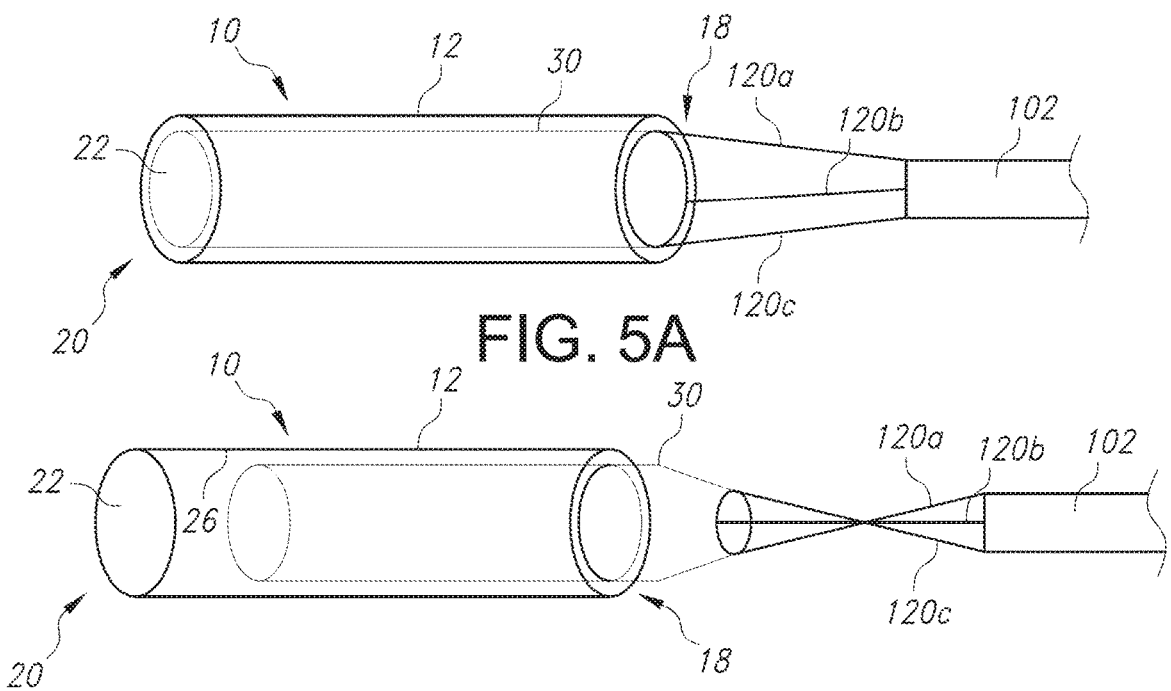
FIG. 5A illustrates a side view of the tool of FIG. 3 being inserted into the endotracheal tube of FIG. 1.
Figure 5B:
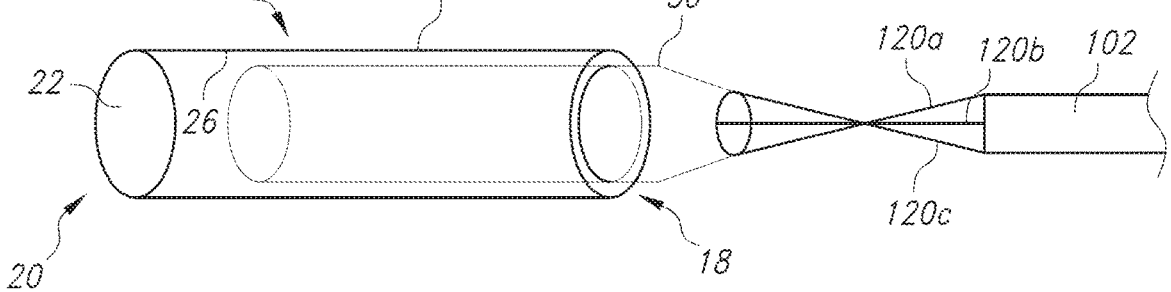
FIG. 5B illustrates a side view of the removal of the telescoping inner sleeve from the endotracheal tube of FIG. 1 using the tool of FIG. 3.

The receiving portions 40 may be located anywhere along the length of the sleeve 30. For instance, as shown in FIG. 5B, the receiving portions 40 may be disposed adjacent to the proximal end 18 of the endotracheal tube 10. In other aspects, the receiving portions 40 may be disposed adjacent to the distal end 20 of the endotracheal tube 10. When the receiving portions 40 are disposed at the distal end 20 of the endotracheal tube 10, the sleeve 30 may be removed from the endotracheal tube 10 by pulling the receiving portions 40 and the end of the sleeve 30 within the lumen 24 such that the sleeve 30 essentially turns inside out within itself. In this manner, no debris or secretions on the sleeve 30 will be shed or aspirated into the airway of the patient.

Figure 3:
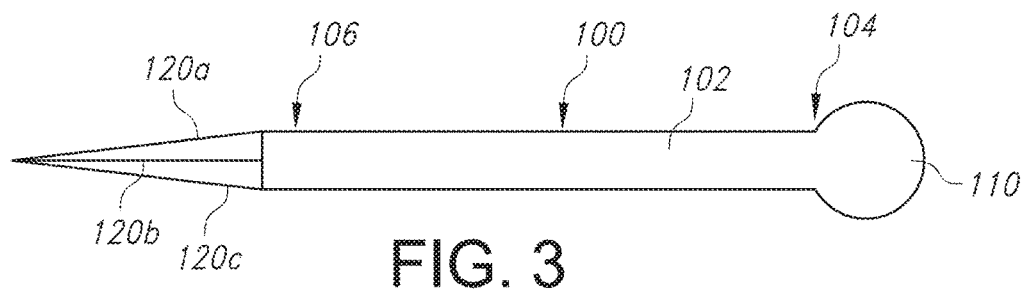
FIG. 3 illustrates a side view of a tool for removing the telescoping inner sleeve from an endotracheal tube.
Figure 4A:
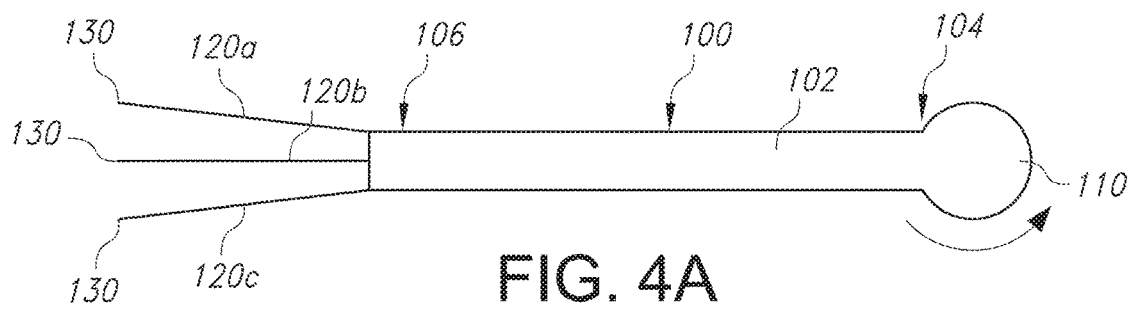
FIG. 4A illustrates a side view of the tool of FIG. 4A when the dial is rotated into the open position.
Figure 4B:
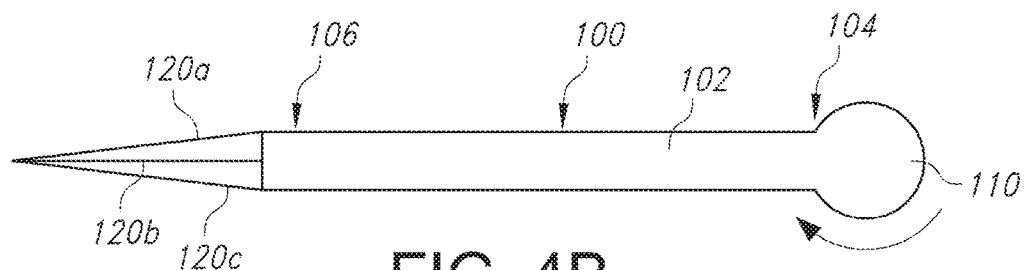
FIG. 4B illustrates a side view of the tool of FIG. 4B when the dial is rotated into the closed position.

As illustrated in FIG. 3, the present invention is further directed to a tool 100 configured for removing the telescoping inner sleeve 30 from an endotracheal tube. The tool 100 includes an elongated body 102 extending from a proximal end 104 to a distal end 106. The tool 102 further includes at least one extension member 120 disposed at the distal end 106 of the elongated body. The at least one extension member 120 is configured to couple to the telescoping internal sleeve 30 of the endotracheal tube 10 for removal of the telescoping internal sleeve 30 from the endotracheal tube 10. The tool 100 may additionally include a handle 110 configured to control movement of the at least one extension member 120. In some aspects of the invention, the at least one extension member 120 may include a plurality of extension members, such as a first extension member 120a, second extension member 120b, and third extension member 120c as shown in FIGS. 3 and 4A-B. The at least one extension member 120, e.g., each of the extension members 120a, 120b and 120c, may further include a coupling portion 130 located at a distal end of each respective extension member.

FIG. 3 shows the tool 100 with the extension members 120a, 120b and 120c in a closed, unused, i.e., resting, position in which the extension members 120a, 120b and 120c are retracted inward at their distal ends 122 (see FIG. 7) where their coupling portions 130 are located. The handle 110 may be actuated in order to deploy the extension members 120a, 120b and 120c into an open, i.e., sleeve-grabbing, position. For instance, the handle 110 may include a dial which rotates in a first direction to deploy the extension members 120a, 120b and 120c into the open position shown in FIG. 4A. Similarly, the dial of handle 110 may be rotated in an opposite, second direction to retract the extension members 120a, 120b and 120c into a closed, sleeve-retraction position. For example, the tool 100 may be inserted within an endotracheal tube 10 in the closed position shown in FIG. 3, then actuated to deploy the extension members 120a, 120b and 120c into the open position when the coupling portion 130 is near the proximal end 18 of the tube body 12, as shown in FIG. 5A. Then, the extension members 120a, 120b and 120c can be retracted into the closed position when coupled to the telescoping inner sleeve 30, as shown in FIG. 5B, in order to initiate the removal of the telescoping inner sleeve 30 from the tube body 12.

Figure 7:
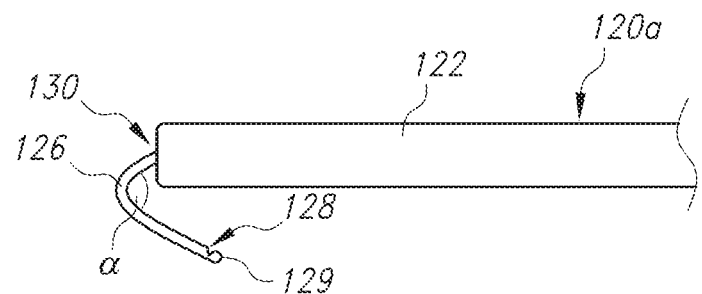
FIG. 7 illustrates a side view of one embodiment of the distal end of the extension members of the tool of FIG. 3.

FIG. 7 illustrates one embodiment of an extension member 120a having a coupling portion 130 with a hook 126, however, notably, each of the extension members 120 may have a coupling portion 130 as illustrated in FIG. 7. The coupling portion 130 is disposed at the distal end 122 of the extension member 120a. The hook 126 extends from the distal end 122 in a first direction extending away from the distal end 122, then bends at an angle alpha ($\alpha$) and extends in a second direction back towards the distal end 122 of the extension member 120a. The angle alpha ($\alpha$) may be greater than about 90 degrees and less than about 180 degrees. For instance, the angle alpha ($\alpha$) may be in a range from about 100 degrees to about 160 degrees, such as from about 120 degrees to about 150 degrees. The hook 126 may further include an indent 128 which may form a grabbing feature at the distal end 129 of the hook 126. The hook 126 may be configured to be inserted through the aperture 42 of the sleeve tabs 40 in order to grab a sleeve tab 40 to remove the sleeve. In some aspects, the hook 126 may be formed from a magnetic material and the sleeve tabs 40 may be formed from a magnetic material in order to facilitate the connection between the hooks 126 and the sleeve tabs 40.

Figure 8:
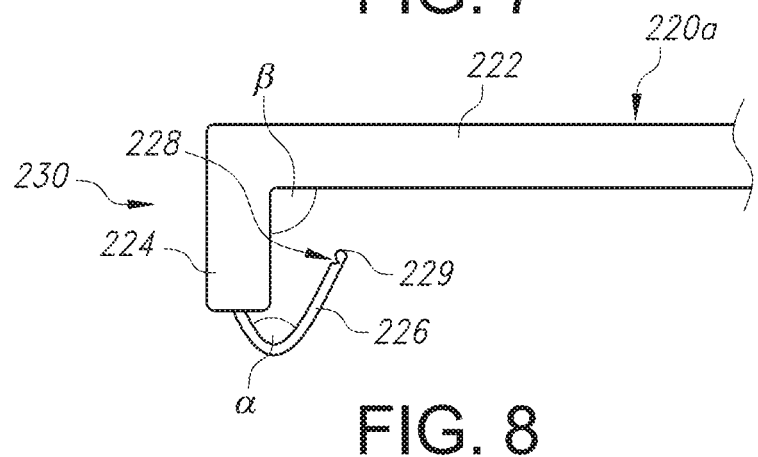
FIG. 8 illustrates a side view of another embodiment of the distal end of the extension members of the tool of FIG. 3.

FIG. 8 illustrates a variation of an extension member 220a having a coupling portion 230 with a hook 226. The coupling portion 230 extends from the distal end 222 of the extension member 220a and include a protrusion 224 extending from the distal end 222 at an angle beta ($\beta$). For instance, the protrusion 223 may extend generally perpendicular to the extension member 220a, e.g., at an angle $\beta$ of about 90 degrees. However, the angle $\beta$ may be any angle from about 20 degrees to about 150 degrees, such as from about 45 degrees to about 135 degrees, or from about 60 degrees to about 120 degrees. Similarly to the hook 126 of FIG. 7, the hook 226 extends in a first direction extending generally away from the protrusion 224 and then bends at an angle $\alpha$ in a second direction extending back toward the protrusion 224 and the distal end 222 of the extension member 220*a*. The hook 226 may also include an indent 228 which may form a grabbing feature at the distal end 229 of the hook 226.

Figure 9:
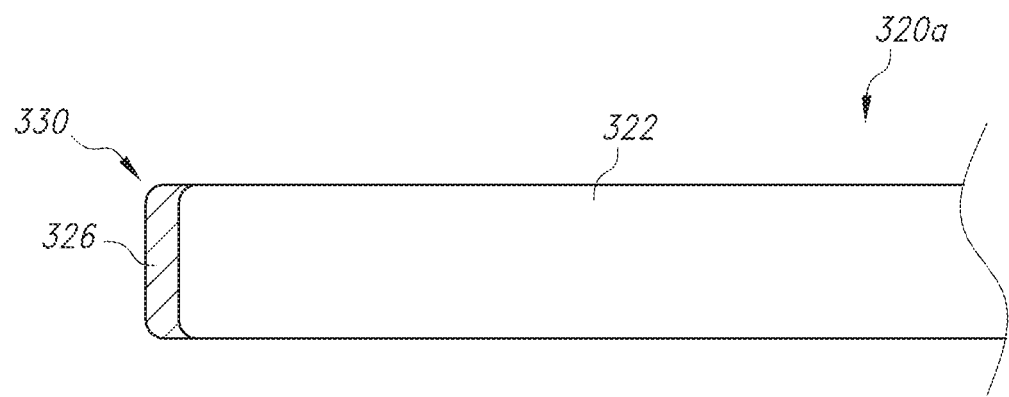
FIG. 9 illustrates a side view of an additional embodiment of the distal end of the extension members of the tool of FIG. 3.
Figure 10:
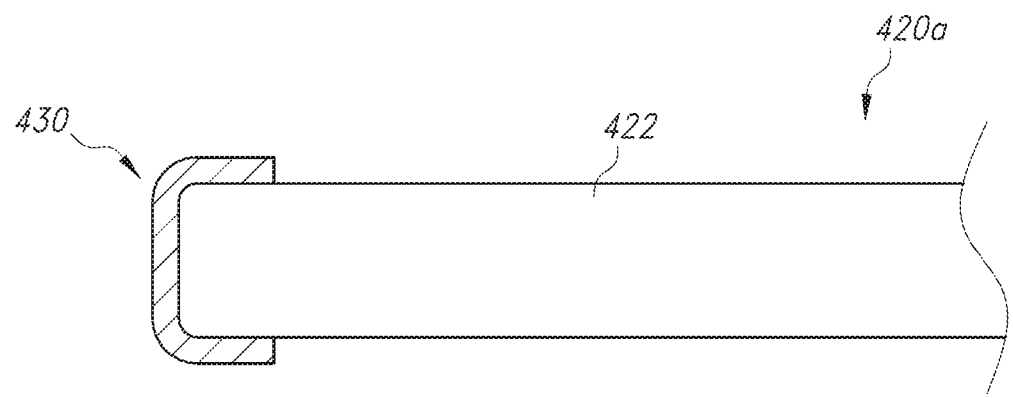
FIG. 10 illustrates a side view of a further embodiment of the distal end of the extension members of the tool of FIG. 3.

In further embodiments, as illustrated in FIGS. 9-10, the extension member may include a coupling portion disposed at the distal end of the extension member without a hook feature. For instance, extension member 320*a* shown in FIG. 10 includes a coupling portion 330 disposed at the distal end 322 of the extension member 320*a*. Similarly, the extension member 420*a* shown in FIG. 11 includes a coupling portion 430 surrounding and/or covering the distal end 422 of the extension member 420*a*. The coupling portions 330 and 430 may be formed from any suitable attachment mechanism that may couple the coupling portions 330 and/or 430 with the sleeve tabs 40. For instance, the coupling portions 330 and/or 430 may be formed from a magnetic material and the sleeve tabs 40 may be formed from a magnetic material in order to facilitate the connection between the coupling portions 330 and/or 430 and the sleeve tabs 40. Additionally or alternatively, the coupling portions 130, 230, 330, 430 may be formed with an adhesive material configured to contact and adhere to the sleeve tabs 40.

Together, the endotracheal tube 10 having a removable telescoping sleeve 30 and the tool 100 for removing the sleeve 30 from the endotracheal tube 10 form a system for maintaining airway patency. By using the tool 100, the removable telescoping sleeve 30 can be removed from the endotracheal tube 10, thereby removing any buildup of microorganisms, biofilm and/or secretions and exposing a fresh, undisturbed, uncontaminated and potentially sterile airflow-effacing surface. Thus, the patency of the airway can be maintained without blocking or interrupting the airflow of ventilation when the endotracheal tube 10 is in use.

The present invention is further directed to a method of maintaining patency and removing deposits from an endotracheal tube, e.g., the endotracheal tube 10. The tool 100 may be inserted into an endotracheal tube assembly, e.g., through a multi-port (not illustrated) that is connected to the endotracheal tube 10 and configured not to break or interrupt the circuit of ventilation. When the tool 100 is inserted into the endotracheal tube assembly, the extension members, e.g. 120*a*, 120*b*, 120*c*, may be in the closed position shown in FIG. 3 such that the tool 100 maintains a streamlined profile. When the tool 100 reaches the endotracheal tube 10, and specifically, the sleeve tabs 40 of the sleeve 30 within the endotracheal tube 10, a user may actuate the tool 100 to deploy the extension members 120*a*, 120*b*, 120*c* into an open or grasping position shown in FIG. 4B. This actuation may occur via rotation of a dial on the handle 110 of the tool 100 or by any other means capable of expanding the extension members 120*a*, 120*b*, 120*c* into the grasping position. Then, the coupling portions of each respective extension member, e.g., coupling portions 130, 230, 330 or 430 may be coupled with the sleeve tabs 40. After coupling the extension members 120*a*, 120*b*, 120*c* with each of the sleeve tabs 40, the extension members 120*a*, 120*b*, 120*c* are retracted back into the closed position as shown in FIGS. 4B and 5B, such as by rotating the dial on the handle 110 in an opposite direction of rotation. Finally, the sleeve 30 is pulled out of the endotracheal tube 10 by withdrawing the tool 100 back out from the endotracheal tube assembly, as shown in FIG. 5B. By withdrawing the sleeve 30 from the endotracheal tube 10, any secretions or deposits on the sleeve 30 are removed from the ventilation circuit, thereby opening up the endotracheal tube 10 and maintaining airway patency.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A tool for removal of a telescoping internal sleeve from an endotracheal tube, the tool comprising:
   an elongated body having a proximal end and a distal end;
   a handle located at the proximal end of the elongated body; and
   at least one extension member disposed at the distal end of the elongated body, the at least one extension member comprising a coupling portion at a distal end of the at least one extension member, the coupling portion comprising a magnetic attachment configured to couple to a magnetic receiving tab of the telescoping internal sleeve of the endotracheal tube for removal of the telescoping internal sleeve from the endotracheal tube.

2. The tool of claim 1, wherein the at least one extension member comprises three extension members.

3. The tool of claim 1, wherein the handle comprises a dial configured to rotate, wherein rotation of the dial in a first direction causes the at least one extension member to be moved into an open position and wherein rotation of the dial in a second direction causes the at least one extension member to be moved into a closed position.

4. The tool of claim 3, wherein in the open position, the at least one extension member is configured to initiate coupling to the telescoping internal sleeve.

5. The tool of claim 3, wherein when the dial is rotated from the open position to the closed position, the at least one extension member is configured to retain the telescoping internal sleeve to retract the telescoping internal sleeve from the endotracheal tube.

6. The tool of claim 1, wherein the at least one extension member comprises a hook extending from a distal end of the at least one extension member.

7. The tool of claim 6, further comprising a protrusion extending from the distal end of the at least one extension member, wherein the hook extends from the protrusion.

8. The tool of claim 6, wherein the hook is configured to couple to a receiving tab of the telescoping internal sleeve.

9. The tool of claim 6, wherein the hook comprises a magnetic hook.

10. An endotracheal tube airway patency system comprising:
    an endotracheal tube comprising a tube body having a proximal end, a distal end, an inner surface, a distal opening disposed at the distal end of the tube body, a proximal opening disposed at the proximal end of the tube body, and an airflow-effacing surface disposed within the tube body, wherein the airflow-effacing surface comprises a telescoping internal sleeve configured to be removed from the endotracheal tube body, the telescoping internal sleeve having a magnetic receiving tab; and
    a tool for removal of a telescoping internal sleeve from the endotracheal tube body, the tool comprising:
    an elongated body having a proximal end and a distal end;

a handle located at the proximal end of the elongated body; and at least one extension member disposed at the distal end of the elongated body, the at least one extension member comprising a coupling portion at a distal end of the at least one extension member, the coupling portion comprising a magnetic attachment configured to couple to the magnetic receiving tab of the telescoping internal sleeve of the endotracheal tube for removal of the telescoping internal sleeve from the endotracheal tube.

11. The system of claim 10, wherein the telescoping internal sleeve comprises one or more layers which are independently removable from the endotracheal tube body.

12. The system of claim 10, wherein the telescoping internal sleeve is collapsible.

13. The system of claim 10, wherein the telescoping internal sleeve is disposed adjacent to or in contact with the inner surface of the endotracheal tube body to maintain patency of the endotracheal tube.

14. The system of claim 10, wherein removal of the telescoping internal sleeve exposes a sterile surface on the inner surface of the endotracheal tube body.

* * * * *